United States Patent [19]

Imran

[11] Patent Number: 5,379,772
[45] Date of Patent: Jan. 10, 1995

[54] FLEXIBLE ELONGATE DEVICE HAVING FORWARD LOOKING ULTRASONIC IMAGING

[75] Inventor: Mir A. Imran, Palo Alto, Calif.
[73] Assignee: Intelliwire, Inc., Sunnyvale, Calif.
[21] Appl. No.: 122,010
[22] Filed: Sep. 14, 1993
[51] Int. Cl.$^6$ ............................................. A61B 8/12
[52] U.S. Cl. ......................... 128/662.06; 128/662.03
[58] Field of Search ........... 128/660.09, 660.1, 660.03, 128/662.03, 662.06, 4, 772; 360/104, 105, 106, 107

[56] References Cited

U.S. PATENT DOCUMENTS

| | | | |
|---|---|---|---|
| 4,175,275 | 11/1979 | Schaefer | 360/104 |
| 4,215,585 | 8/1980 | Kunii et al. | 128/660.09 |
| 4,421,118 | 12/1983 | Dow et al. | 128/660.1 |
| 4,674,515 | 6/1987 | Andou | 128/662.06 |
| 4,841,979 | 6/1989 | Dow et al. | 128/660.1 |
| 4,869,258 | 9/1989 | Hetz | 128/662.06 |
| 4,895,158 | 1/1990 | Kawabuchi | 128/662.06 |
| 4,917,097 | 4/1990 | Proudian | 128/662.06 |
| 4,930,515 | 6/1990 | Terwilliger | 128/662.06 |
| 4,967,752 | 11/1990 | Blumenthal | 128/660.1 |
| 5,001,185 | 3/1991 | Yock | 128/662.03 |
| 5,024,234 | 6/1991 | Leary | 128/663.01 |
| 5,029,588 | 7/1991 | Yock | 128/662.06 |
| 5,049,130 | 9/1991 | Powell | 604/96 |
| 5,054,492 | 10/1991 | Scribner | 128/662.06 |
| 5,055,101 | 10/1991 | McCoy | 128/772 |
| 5,090,414 | 2/1992 | Takano | 128/662.05 |
| 5,095,911 | 3/1992 | Pomeranz | 128/662.06 |
| 5,100,424 | 3/1992 | Jang | 606/159 |
| 5,108,411 | 4/1992 | McKenzie | 606/159 |
| 5,117,831 | 6/1992 | Jang | 128/662.06 |
| 5,135,486 | 8/1992 | Eberle | 604/96 |
| 5,167,223 | 12/1992 | Koros | 128/20 |
| 5,167,233 | 12/1992 | Eberle | 128/662.06 |
| 5,207,672 | 5/1993 | Roth et al. | 128/660.03 |
| 5,303,105 | 4/1994 | Jorgenson | 360/106 |

FOREIGN PATENT DOCUMENTS 033664 10/1989 European Pat. Off. .... G10K 11/00

*Primary Examiner*—George Manuel
*Attorney, Agent, or Firm*—Flehr, Hohbach, Test, Albritton & Herbert

[57] ABSTRACT

A flexible elongate device comprising a flexible elongate member having proximal and distal extremities, means mounted on the distal extremity and having a cavity therein, a transducer disposed in the cavity, support means for mounting the transducer so that energy omitted from the transducer is propagated in a forward direction, and oscillatory means connected to said support means for parting angular motion to the support means to repeatedly sweep that through an angle, said oscillatory means including at least one shape memory element and means for repeatedly energizing and deenergizing the shape memory element.

10 Claims, 2 Drawing Sheets

FLEXIBLE ELONGATE DEVICE HAVING FORWARD LOOKING ULTRASONIC IMAGING

This invention relates to a flexible elongate device having forward looking ultrasonic imaging.

Ultrasonic probes and catheters have heretofore been provided which are capable of ultrasonic imaging. However, in most of those prior art devices, the imaging was in a direction transverse to the longitudinal axis of the probe or catheter. In U.S. Pat. No. 4,895,158, there is disclosed an ultrasonic probe which looks in a forward direction or distally of the tip of the probe. However, the device is relatively large and bulky and is disclosed as being useful only for the coelom of a body. There is therefore need for a mechanism which can be used in connection with flexible elongate devices of a very small size and which is provided with forward looking capabilities.

In general, it is an object of the present invention to provide a flexible elongate device of a relatively small size which has forward looking ultrasonic imaging capabilities.

Another object of the invention is to provide a device of the above character which utilizes at least one shape memory element for the actuation mechanism.

Another object of the invention is to provide a device of the above character which can be utilized for viewing forwardly in small vessels such as arteries and veins.

Another object of the invention is to provide a device of the above character which can be utilized for imaging the walls of the chamber of the heart.

Another object of the invention is to provide a flexible elongate device of the above character in which various types of transducers can be utilized.

Additional objects and features of the invention will appear from the following description in which the preferred embodiments are set forth in detail in conjunction with the accompanying drawings.

Figure 1:
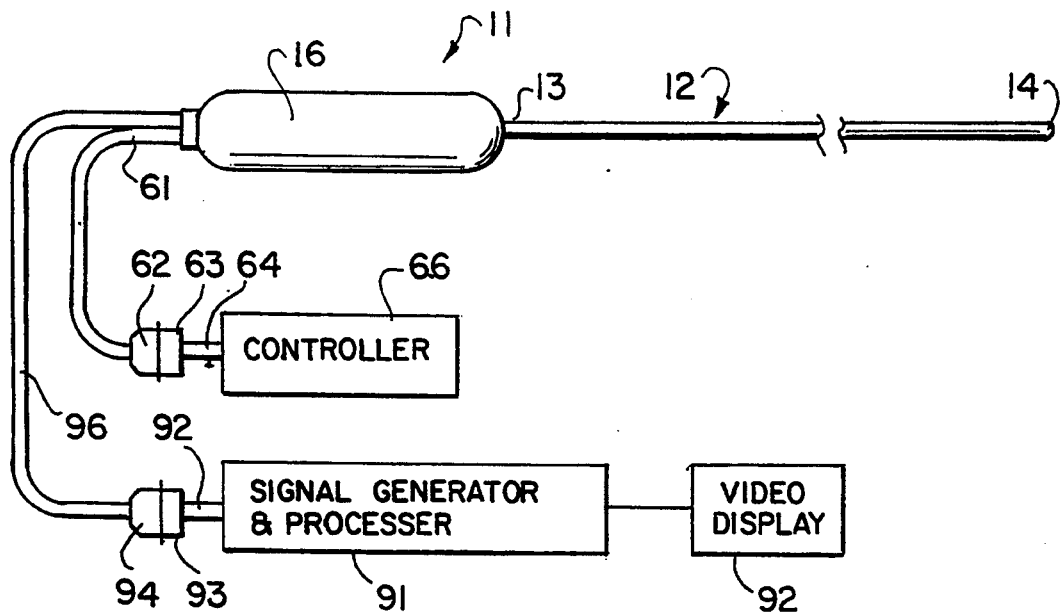
FIG. 1 is the schematic illustration of a flexible elongate device incorporating the present invention.

In general, the flexible elongate device is comprised of a flexible elongate member having proximal and distal extremities. A transducer element is disposed in the distal extremity. Support means is provided for mounting the transducer element. Means is provided for supplying energy to the transducer element. Oscillatory means is connected to the support means for imparting angular motion to the support member to cause the transducer element to sweep through an angle. The oscillatory means includes at least one shape memory element. Means is provided for supplying energy to the shape memory element.

More particularly, as shown in the drawings the flexible elongate device 11 consists of a flexible elongate member 12 having proximal and distal extremities 13 and 14. The flexible elongate member 12 can have a size ranging from a diameter of 0.032 inches to 0.125 inches and preferably approximately 0.095 inches. It can have a suitable length, as for example ranging from 150 to 170 centimeters. A handle 16 adapted to be held by the human hand is provided on the proximal extremity 13.

The flexible elongate member 12 can be formed in a conventional manner. For example, it can be formed of a suitable material such as a plastic with a stainless steel braid therein which can be utilized as a torque tube for supplying rotational motion from the proximal extremity to the distal extremity 14. To impart additional flexibility to the distal extremity, the distal extremity 14 can be formed of a coil spring in a manner well known to those skilled in the art. A tip 21 is secured to the distal extremity 14 and is formed of a material which will transmit the desired energy in a forward direction distally of the tip 21. The tip 21 encloses a cylindrical cavity 22 and has a hemispherical or a rounded forward extremity 23. A transducer 26 is disposed within the cavity 22 and is carried by a support member 27. The transducer 26 can be of any conventional type and size, as for example an ultrasonic transducer having a width of 0.005" and a length of 0.010" to 0.015". When this is the case, the tip 21 is formed of a material which is transparent to ultrasonic energy and has an impedance which matches the transducer and which also matches the body fluid, as for example blood in which the tip 21 may be disposed.

An oscillatory linkage mechanism 31 is provided for moving the support member 27 with the transducer 26 thereon through an angle across the rounded extremity 23. This mechanism consists of a support arm 32 which is pivotally mounted on a shaft 33 extending transversely of the tip 21. The arm 32 is provided with an extension 34 which extends at a suitable angle with respect to the arm 32. This angle is substantially equal to the angle through which the transducer 26 is to be moved, as for example an angle of 70° from a line parallel to the arm 32. This extension arm or rocker arm 34 is pivotally connected to a link 36 at 37 which has its other end pivotally connected by a pin 38 to a circular movable member or disk 39 slidably mounted for longitudinal or axial movement within the cavity 22.

Means is provided on opposite sides of the movable disk 39 for moving the same axially in the cavity 22 and consists of at least one shape memory element and means for activating and deactivating the shape memory element. In this embodiment of the invention the means consists of first and second coil springs 41 and 42 disposed within the cavity 42 on opposite sides of the disk 39 and having one end of each of the same engaging the respective side of the slidable disk 39. The springs 41 and 42 are formed of a suitable shape memory alloy such as Nitinol which have been programmed whereby when they become activated, as for example by the application of heat thereto as hereinafter described, they expand and conversely when energy is no longer supplied to the same, they become soft and easy to compress.

The other end of the first spring 41 engages a disk 46 which is mounted in a fixed position within the cavity 22 whereas the other end of the second spring 42 engages another disk 47 mounted in a fixed position in the cavity 22 on the other side of the slidable disk 39. A hole 48 is provided in the disk 46 to accommodate the movement of the link 36. Conductors 51 are provided which extend from the handle 16 through the proximal extremity 13 of the flexible elongate member 12 up through a hole 52 provided in the fixed disk 47 and then through a hole 53 provided in the slidable disk 39 and extend along the link 36, the extension arm 34 and the arm 32 to both sides of the transducer 26 so that electrical energy can be supplied to the transducer 26 and removed from the transducer 26.

Figure 2:
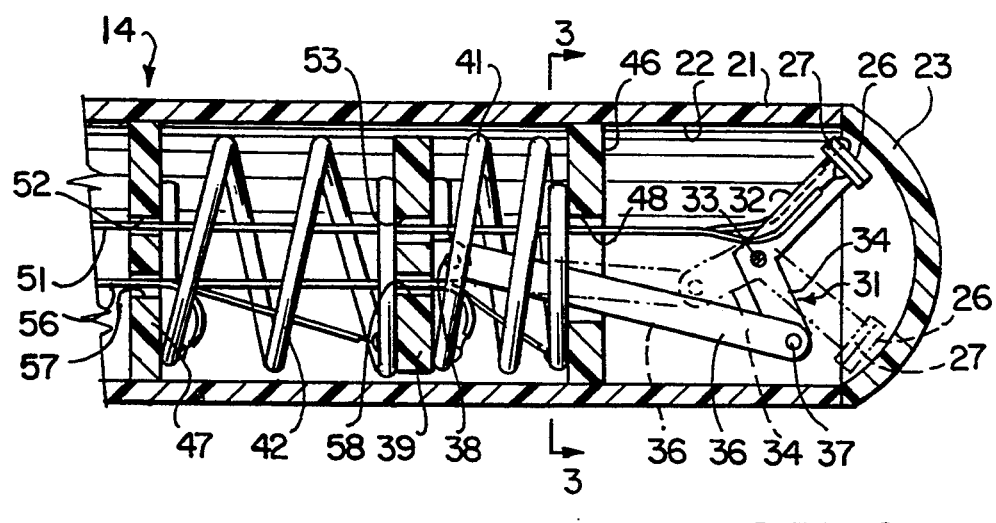
FIG. 2 is a greatly enlarged cross-sectional view of the distal extremity of the device shown in FIG. 1.
Figure 3:
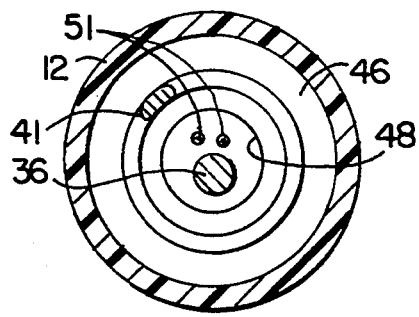
FIG. 3 is a cross-sectional view taken along the line 3—3 of FIG. 2.

An additional group of conductors 56 is provided for making electrical connections to opposite ends of the first and second springs 41 and 42 as shown in FIG. 2 and extend from the handle 16 and through the flexible elongate member 12 through the hole 57 provided in the fixed disk 47 and a hole 58 in the slidable disk 39. The conductors 51 and 56 are connected into a cable 61 which is connected into a connector 62. The connector 62 is connected to a mating connector 63 which is connected to a cable 64 connected to a controller 66.

Figure 4:
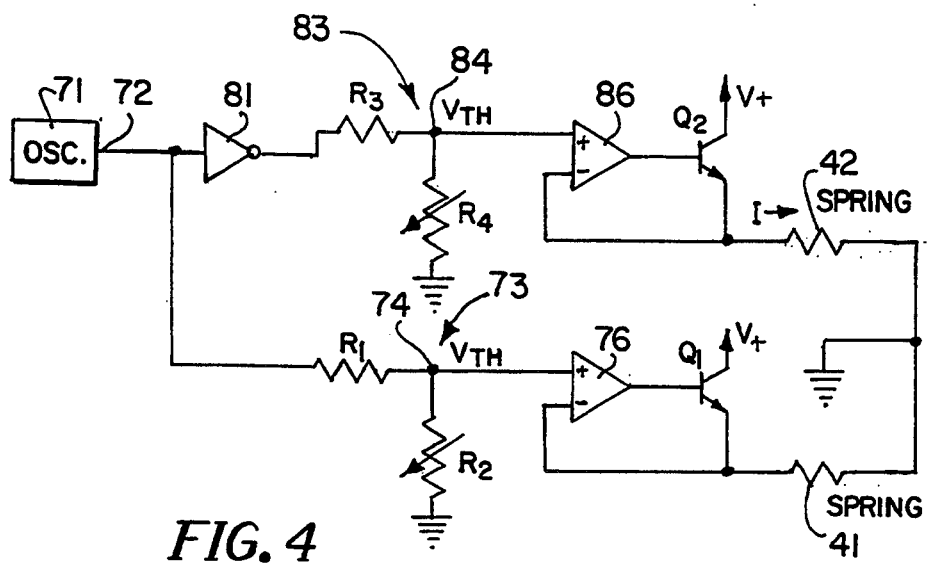
FIG. 4 is a schematic circuit diagram for providing electrical energy for operating the mechanism shown in FIGS. 2 and 3.

The controller 66 can include circuitry of the type as shown in FIG. 4 for supplying energy to the first and second springs 41 and 42 so that these small springs 41 and 42 can be activated and deactivated in short periods of time in the range of a millisecond to obtain oscillatory movement within the range of 100 to 200 Hz but which range could be extended from 10 to 1,000 Hz. Thus there is provided an oscillator 71 that provides an oscillatory output of the desired frequency range from 10 to 1,000 Hz in the form of a square wave on an output 72. This output is connected through a resistive divider 73 consisting of a series resistors R1 connected to a junction 74 and an adjustable resistor R2 connected between the junction and ground and connected to the input of an operational amplifier 76 which has its output connected to the base of a transistor Q1 having the collector connected to a source of a suitable voltage, as for example five volts as indicated by V+ and its emitter connected to the minus input of the amplifier 76. The emitter is also connected to one side of the spring 41 and the other side of the spring 41 is connected to ground as shown. Similarly, the output 72 from the oscillator 71 is connected through an inverter 81 to invert the square wave by 180° and supplies the same through a resistive network 82 similar to the resistive network 73 consisting of a series resistor 83 connected to a junction 84 through an adjustable resistor R4 to ground. The junction 84 is also connected to the plus terminal of an operational amplifier 86 which has its output connected to the base of a transistor Q2 which is connected to a suitable V+ voltage as in Q1 and has it emitter connected to the minus terminal of the operational amplifier 86. The emitter is also connected to one end of the spring 42 and the other end of the spring 42 is connected to ground as shown. Thus it can be seen that an inverted output is supplied to the spring 42 whereas a noninverted output from the oscillator 71 is supplied to the spring 41. Controls (not shown) can be provided in the controller 66 or in the handle 16 for controlling the output frequency from the oscillator 71 and for also for controlling the two currents supplied to the springs 41 and 42 to cause the rapid oscillation of the transducer 26 across the face of the rounded extremity 23.

During the time this oscillation is occurring, signals are supplied from the signal generator 91 through a cable 92 through mature connectors 93 and 94 connected to a cable 96 connected to the handle 16 and thence through the conductors 51 to the transducer 26 which converts the electrical signals to ultrasonic signals. The ultrasonic signals are directed forwardly or axially in a scanning motion through the rounded extremity 23 to see what is being encountered as the flexible elongate device 11 is advanced into a vessel, as for example an artery or a vein. Reflections or echoes which are produced will be picked up by the transducer 26 and converted to electrical signals which are returned to the signal processor 91 and displayed on a video display 92.

Because the springs 41 and 42 have such a low mass, they can be energized and deenergized to cause expansion by one of these springs and relaxation of the other spring and thereafter expansion of the other spring and relaxation of the one spring to cause rapid oscillatory movement of the slidable disk 39 within the tip 21. This rapid oscillatory sliding movement of the disk is translated through the lever arm linkage to cause rapid oscillatory or harmonic motion of the transducer 26 across the face of the rounded extremity 23. It should be appreciated that other waveforms such as a substantially linear ramp or triangular wave may be used to drive the springs to cause the angular velocity of the transducer to vary during each cycle.

The flexible elongate device can be introduced into a body cavity, as for example a vessel in a patient such as an artery or a vein in a conventional manner and advanced therein by use of the handle 16. It should be appreciated that in connection with the present invention steering capabilities can be provided for the distal extremity 14 to facilitate navigation of tortuous vessel such as that described in U.S. Pat. No. 5,238,005.

Although the present invention has been described principally in connection with the use of ultrasound, it should be appreciated that the principles of the present invention can be utilized in other flexible elongate devices in which it is desired to provide diagnostic and therapeutic procedures forward of the distal extremity of the device. For example such rapid oscillatory motion can be utilized in connection with an optical device to provide diffuse heating forward of the distal extremity rather than pin point heating.

Figure 5:
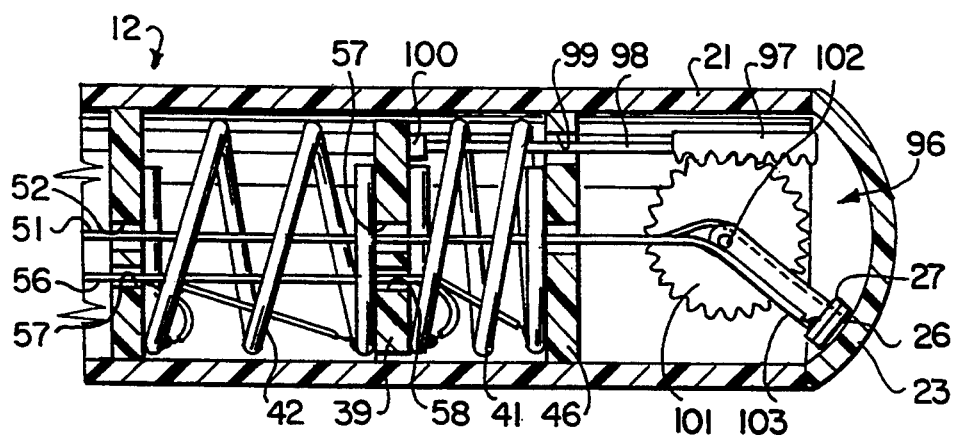
FIG. 5 is a greatly enlarged cross-sectional view of the distal extremity of the device shown in FIG. 1 showing another embodiment of actuation mechanism.

Another embodiment of a mechanism for causing rapid oscillatory or harmonic motion of a transducer at the distal extremity of a flexible elongate device 11 is shown in FIG. 5. It in many respects is similar to the mechanism shown in FIG. 2 but the linkage provided in FIG. 2 has been replaced by a rack and pinion assembly 96 consisting of a rack 97 carried by a rod 98 extending through a hole 99 in the fixed disk 46 and secured at 100 to the movable disk 39 and the rack 97 has its teeth engaging a pinion 101 rotatably mounted on a shaft 102 extending transversely of the tip 21. The pinion 101 has a support arm 103 mounted therein which corresponds to the support arm 32 and is connected to the support member 27 carrying the transducer 26.

The operation of the embodiment of the invention shown in FIG. 5 is very similar to that shown in FIG. 2 in that the oscillatory motion of the movable disk 39 is translated to the transducer 26 by rack and pinion assembly 96 rather than the linkage mechanism 31 shown in FIG. 2. It can be seen as the springs 41 and 42 are energized and deenergized in accordance with the circuitry shown in FIG. 4, that the rack 97 will be reciprocated back and forth to cause a reciprocatory movement of the pinion 101 to cause the arm 103 carried thereby to move the transducer 26 across the face of the rounded extremity 23 in a manner substantially identical to that described in conjunction with the embodiment shown in FIG. 2.

The transducer 26 can have a suitable size, as for example a width of 0.005 inches and a length of 0.010 to 0.015 inches.

Figure 6:
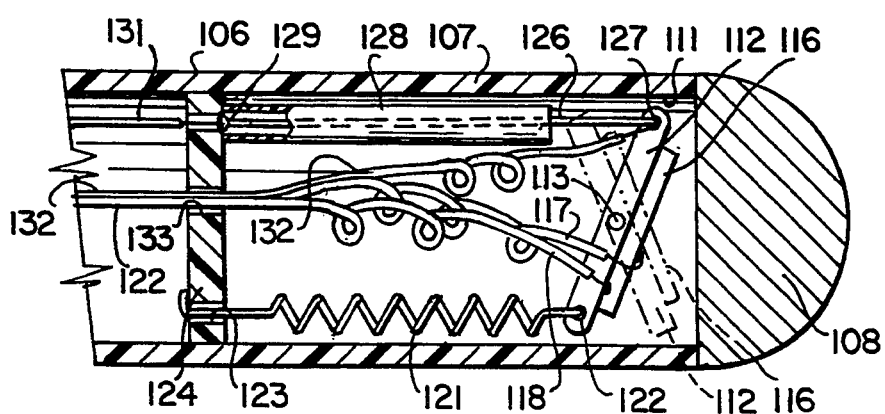
FIG. 6 is a greatly enlarged cross-sectional view of the distal extremity of the device shown in FIG. 1 showing still another embodiment of the mechanism for use therein.

Still another embodiment of a mechanism for achieving oscillatory motion of a transducer at the distal extremity of a flexible elongate element is shown in FIG. 6 in which a flexible elongate element 106 is provided which has a distal extremity 107 having a rounded hemispherical lens 108 mounted thereon which is transparent to ultrasonic energy and which is formed of a material which is impedance matched to the ultrasonic energy and to a liquid, as for example blood in which it is immersed. A cylindrical cavity 111 is provided proximal of the lens 108. A support member 112 is pivotally mounted on a shaft 113 mounted transversely of the distal extremity 107 and carries a transducer 116 of a suitable type such as an ultrasonic transducer which faces in a direction towards the hemispherical lens 108. Conductors 117 and 118 are connected to the front and back sides of the transducer and extend to the proximal extremity (not shown).

Means is provided for imparting rocking or oscillatory motion of the support member 112 so it rotates through a suitable angle, as for example an angle of 60° to 90° and consists of a tension spring 121 which has one end 122 connected to one end of the support member 112 and has the other end 123 secured to a stationary disk 124 mounted in the cavity 111 and secured to the flexible elongate member 106 in a suitable member such as by an adhesive (not shown).

A shape memory element 126 formed of a suitable material such as Nitinol and having a negative coefficient of expansion has one end 127 secured to the support member 112 opposite the end where the end 122 of the spring 121 is secured. The element 126 extends through a flexible sleeve 128 which extends to the disk 124 and is mounted thereon. It should be appreciated that if desired, the sleeve 128 can be omitted. The other end 129 of the shape memory element 126 is secured to the fixed disk 124 by suitable means such as an adhesive and is connected to a conductor 131 which extends to the proximal extremity of the flexible elongate member 106. The other end 127 is also connected to a conductor 132 extending through a hole 133 in the disk 124 and also extends to the proximal extremity (not shown) of the flexible elongate member 106 where it can be connected to the power supply and controller so that oscillatory current can be supplied to the shape memory element 126. The conductors 117 and 118 can extend through the same hole 133 as shown. The application of electrical energy to the element 126 will cause the element 126 to shrink to pull that end of the support member to which it is attached in a proximal direction against the yieldable force supplied by the spring 121 to cause the transducer 116 to be moved through a desired angle, as for example 60° to 70°. As soon as the element 126 is deenergized, it will cool and relax and permit the transducer 116 to be returned to its initial position shown in FIG. 6 under the force of the spring 121. Thus, it can be seen that repeated energization and deenergization of the shape memory element 126 will cause oscillatory or harmonic motion of the transducer 116 to cause ultrasonic energy to be transmitted through the hemispherical lens 108 in a sweeping motion to sweep the space immediately in front of the hemispherical lens 108 so that it echos or reflections which are created can be received by the transducer 116 and supplied to a signal processor and generator 91 of the type hereinbefore described and the results displayed on a video display 92.

From the foregoing it can be seen that there has been provided a flexible elongate device 11 which can be made in very small sizes so that it can be introduced into small vessels, as for example the arterial and venus vessels of the heart to permit forward looking imaging in the vessel. Such forward looking imaging will give the conformation of the stenosis occurring in the vessel. It should be appreciated that the flexible elongate device of the present invention can be utilized in conjunction with other instruments or devices. For example it could be used with a laser angioplasty catheter to ensure that the laser beam be properly directed within the vessel. The mechanisms which are provided to achieve the oscillatory motion are of the type which are very compact and can be utilized in applications having very little space, as for example the distal extremity of small flexible elongate devices such as catheters and guide wires.

What is claimed is:

1. A device for insertion into a vessel of a patient comprising a flexible elongate member having proximal and distal extremities and having sufficient flexibility so that it can be advanced into the vessel, means mounted on the distal extremity and having an enclosed cavity therein, a transducer disposed in the cavity and emitting energy, support means for mounting the transducer so that energy emitted from the transducer is propagated in a forward direction, oscillatory means connected to said support means for imparting angular motion to the support means to repeatedly sweep said support means and the transducer carried thereby through an angle in said forward direction, said oscillatory means including at least one shape memory element made from a shape memory alloy and means for repeatedly activating and deactivating the shape memory element.

2. A device as in claim 1 wherein said support means includes a support member having first and second sides and wherein said at least one shape memory element is connected to the support member at one point together with spring means connected to the support member at a point spaced laterally away from the point at which the at least one shape memory element is connected and applying a yieldable force thereto whereby upon repeated activation and deactivation of the shape memory element, the support member is moved against the yieldable force of the spring means.

3. A flexible elongate device comprising a flexible elongate member having proximal and distal extremities, means mounted on the distal extremity and having a cavity therein, a transducer disposed in the cavity, support means for mounting the transducer so that energy emitted from the transducer is propagated in a forward direction and oscillatory means connected to said support means for imparting angular motion to the support means to repeatedly sweep said support means and the transducer carried thereby through an angle in said forward direction, said oscillatory means including at least one shape memory element made from a shape memory alloy and means for repeatedly activating and deactivating the shape memory element, said at least one shape memory element comprising first and second shape memory elements in the form of first and second springs disposed within said cavity and a movable member disposed between the first and second springs and engaging the first and second springs, means mounted within the cavity for affixing the other ends of the first and second springs so that upon activation and deactivation of the first and second springs the movable member is reciprocated axially of the cavity and a mechanism connected to said movable member and said support means for the transducer for repeatedly moving the transducer carried thereby through said angle.

4. A device as in claim 3 wherein said mechanism is in the form of a linkage mechanism.

5. A device as in claim 3 wherein said mechanism is in the form of a rack and pinion mechanism.

6. A device as in claim 3 wherein said means for repeatedly activating and deactivating the shape memory element includes means for electrically energizing and deenergizing the shape memory element.

7. A device as in claim 6 wherein said means for repeatedly activating and deactivating the first and second shape memory elements also includes circuitry supplying electrical pulses to said first and second shape memory elements 180° out of phase with each other.

8. A device as in claim 7 wherein said transducer is oscillated at a frequency ranging from 10 to 1000 Hz.

9. A flexible elongate device comprising a flexible elongate member having proximal and distal extremities, means mounted on the distal extremity and having a cavity therein, a transducer disposed in the cavity, support means for mounting the transducer so that energy emitted from the transducer is propagated in a forward direction and oscillatory means connected to said support means for imparting angular motion to the support means to repeatedly sweep said support means and the transducer carried thereby through an angle in said forward direction, said oscillatory means including at least one shape memory element made from a shape memory alloy and means for repeatedly activating and deactivating the shape memory element, said transducer being an ultrasonic transducer, said means mounted on the distal extremity forming a cavity which is transparent to ultrasonic energy.

10. A medical device for insertion into a vessel of a patient comprising a flexible elongate member having proximal and distal extremities, means substantially transparent to ultrasonic energy mounted on the distal extremity and providing an enclosed cavity therein, a transducer emitting ultrasonic energy disposed in the cavity, support means for mounting the transducer so that ultrasonic energy emitted from the transducer is propagated out of the cavity in a forward direction away from the distal extremity, and oscillatory means connected to said support means for imparting angular oscillatory motion to the support means to repeatedly sweep said support means and the transducer carried thereby through an angle in said forward direction, said oscillatory means including at least one element made from a shape memory alloy and means for repeatedly activating and deactivating the shape memory alloy of the element.

* * * * *